United States Patent [19]

Salimbeni et al.

[11] Patent Number: 5,059,601
[45] Date of Patent: Oct. 22, 1991

[54] IMIDAZOLONE DERIVATIVES WITH ACTIVITY ON CENTRAL NERVOUS SYSTEM AND ANTIHYPERTENSIVE ACTIVITY, PREPARATION METHODS THEREOF, AND PHARMACEUTICAL COMPOSITIONS CONTAINING THEM

[75] Inventors: Aldo Salimbeni; Giuseppe Cascio; Elso Manghisi, all of Milan, Italy

[73] Assignee: Istituto Lusofarmaco D'Italia S.P.A., Milan, Italy

[21] Appl. No.: 467,000

[22] Filed: Jan. 18, 1990

[30] Foreign Application Priority Data

Jan. 25, 1989 [IT] Italy ................................ 19193 A/89

[51] Int. Cl.$^5$ ................. A61K 31/495; A61K 31/445; C07D 403/00; C07D 401/00
[52] U.S. Cl. .................................... 514/255; 546/210; 544/370; 514/326
[58] Field of Search ........................ 546/210; 544/370; 514/326, 255

[56]  References Cited

U.S. PATENT DOCUMENTS 4,329,471  5/1982  Grisar ................... 546/210
4,381,393  4/1983  Grisar ................... 544/370
4,889,864  12/1989  Ehrhardt et al. ........... 546/210

Primary Examiner—Mary C. Lee
Assistant Examiner—Robert C. Whittenbaugh
Attorney, Agent, or Firm—Walter H. Schneider

[57]  ABSTRACT

Invention concerns 4,5-bisubstituted-2-imidazolone derivatives of formula I

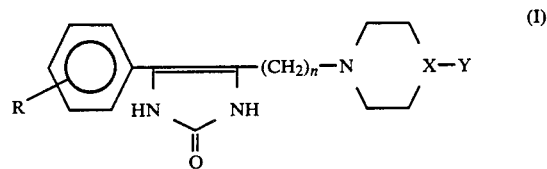

and pharmaceutically acceptable salts thereof, having high affinity in vitro for $D_2$, 5-$HT_{2, 1}$ receptors and in vivo activity on central nervous system and antihypertensive activity with negligible secondary effects; methods for the preparation thereof; pharmaceutical formulations containing them.

6 Claims, No Drawings

IMIDAZOLONE DERIVATIVES WITH ACTIVITY ON CENTRAL NERVOUS SYSTEM AND ANTIHYPERTENSIVE ACTIVITY, PREPARATION METHODS THEREOF, AND PHARMACEUTICAL COMPOSITIONS CONTAINING THEM

The present invention concerns compounds of general formula I

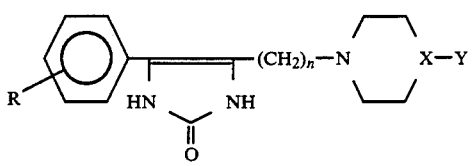

wherein:

R is a halogen atom, a straight or branched $C_1$–$C_4$ alkoxy group or a $C_1$–$C_4$ alkyl group;

n is an integer from 1 to 3;

x is a nitrogen atom forming a piperazine ring in which case Y may be a $C_1$–$C_4$ alkyl group optionally substituted by a hydroxy group; a phenyl group optionally substituted by one or more halogen atoms (as fluorine, chlorine or bromine), $C_1$–$C_4$ alkoxy group or by hydroxy group;

or X is a CH group and Y is then hydrogen, phenyl, benzoyl, benzamido, 2-oxo-1-benzimidazolinyl groups which are optionally substituted by one or more halogen atoms.

Preferred meanings for Y when X is a nitrogen atom are 2-hydroxyethyl, 3-hydroxypropyl, 2-methoxyphenyl, 2-hydroxyphenyl, phenyl, methyl, ethyl.

A halogen atom is preferably a chlorine, fluorine or bromine atom.

The present invention concerns also salts of compounds with pharmaceutically acceptable inorganic or organic acids as hydrochloric, hydrobromic, nitric, sulphoric, phosphoric, acetic, propionic, maleic, fumaric, malic, tartaric, citric, methansulphonic acid etc. The invention concerns also the processes for the preparation of the compounds of general formula I.

The compounds of the present invention can be prepared, for example, by reacting a compound of formula

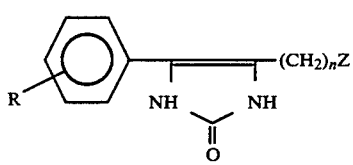

wherein Z is a halogen atom (e.g. bromine, chlorine) or a group of formula $R_1SO_2O$—(wherein $R_1$ is a $C_1$–$C_4$ alkyl, phenyl or p-tolyl group), R and n are as defined above, with an amine of formula III

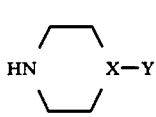

wherein X and Y are as defined above.

Reaction of compounds II with amines III can be carried out in suitable solvent (e.g. methanol, ethanol, dioxane, acetonitrile, tetrahydrofurane, N,N-dimethylformamide, N,N-dimethylacetamide, methylene chloride, dimethylsulphoxide). The reaction temperature ranges between 0° C. and 150° C. according to the boiling-point of the solvent. In order to neutralize the inorganic or organic acid (HZ) released from the reaction either an excess base III or an organic base (as sodium or potassium carbonate) can be added.

The starting products II can be prepared by reaction of the correspondent known -bromo- -chlorobutyrophenones with ethyl potassium N-cyano-carbammate and followed by acid hydrolysis of the intermediate product, according to the method described by T. Taguchi and others, Chem. Letters, 401 (1974).

The compounds object of the present invention of formula I have interesting pharmacological properties.

Said compounds have in vitro good affinity against $D_2$, 5-$HT_2$, $\alpha 1$ receptors determined towards [3H]Spiperone, [3H]-ketanserine, and [3H]-prazosine respectively, using the methods described by Y.Z. Fields, R.D. Reisine, H.I. Yamamura, Brain Research 136, 578 (1977); Y.E. Leysen, C.Y.E. Nyemegers, Y.M. Van Neuten, P.M. Endladurong, Mol Pharmacol. 21, 322 (1981); P. Greengrass, R. Bremner, Eur. J. Pharmacol. 55, 323 (1979). They show a reduced toxicity in vivo, a good activity on central nervous system in various behaviour tests (e.g. stereotypy caused by apomorfine, central dopaminergic neuronal firing) and a good antihypertensive activity (determined in SHR rat after oral administration using the method reported by J. Pfeffer and others, J. Lab. Clin. Med. 78, 957 (1971)).

The biological properties of the compound 4-(4-fluorophenyl)-1,3-dihydro-5[4-(2-methoxyphenyl)-1-piperazinyl)ethyl]2H-imidazol-2-one (described in example 2) are reported herebelow.

This compound has an $IC_{50}$ of $4,7.10^{-9}$ for $D_2$ receptors, $5,2.10^{-8}$ for 5-$HT_2$ receptors, $4,5.10^{-8}$ for $\alpha_1$ receptors, and a toxicity in rat expressed as $DL_{50} > 2000$ mg/kg/os and gives a decrease in systolic pressure of about 21% at a dose of 10 mg/kg/os.

The compounds object of the present invention may be, therefore, used as antipsychotic, antidepressive, ansiolytic drugs or in preventive treatment and in therapy of hypertension and other cardiovascular diseases (ischaemic cardiopathies, thrombosis, cerebral circulation disorders etc.). The compounds of the present invention are slightly toxic, and well absorbed orally and when utilized as drugs, as reported above, can be administered, orally or parenterally, alone or in mixture with suitable carriers, excipients or diluents in different pharmaceutical compositions, as powders, granulates, tablets, capsules or injectable solutions.

While dosage ranges according to the conditions of the disease to be treated and the administration way, the compounds of formula I are administered orally as individual dosis ranging from 0,1 to 10 mg/kg, preferably from 0,3 to 3 mg/kg, or i.v. as individual dosis from about 0,003 to 0,1 mg/kg, preferably from 0,01 to 0,1 mg/kg 2-3 times daily, e.g. for hypertensive adult.

The following examples illustrate the invention without limiting it. The identity and purity of the substances were detected by elementary chemical analysis (C,H,N) and IR spectroscopy, UV, NMR and mass spectrography.

EXAMPLE 1

3-(2-chloroethyl)-4-(4-fluorophenyl)-1,3-dihydro-2H-imidazol-2-one

A mixture of 2-bromo-4-chloro-1-(4-fluorophenyl)-butan-1-one (197 g, 0,7 moles), ethyl potassium N-cyanocarbamate (108 g, 0,7 moles) in acetonitrile 1,7 l was refluxed for 8 hours, after cooling, solid was filtered off and mother liquor dried. The residue was dissolved in CH$_3$OH and this solution added dropwise to a 3,3N HCl solution in CH$_3$OH (400 ml) at 10° C.

The mixture was left at room temperature for 0,5 hour, the obtained solid was filtered after 24 h (116 g, m.p. 182–184° C.) and treated with a solution of 5,5M HCl in CH$_3$OH (1,1 l), then refluxed for 4 hours. The solvent is eliminated in vacuum and residue diluted in isopropylic acid, then filtered. Yield 75 g; m.p. 151–154° C.

3-(2-chloroethyl)-4-(4-chlorophenyl)-1,3-dihydro-2H-imidazol-2-one;

3-(3-chloropropyl)-4-(4-fluorophenyl)-1,3-dihydro-2H-imidazol-2-one are prepared according to the above process.

EXAMPLE 2

A solution of 1,5 g (0,006 mole) of 3-(2-chloroethyl)-4-(4-fluorophenyl)-1,3-dihydro-2H-imidazol-2-one and 2,6 g (0,012 mole) of 4-(2-hydroxy-ethyl)piperazine in anhydrous DMF 10 ml is heated at 70° C., in presence of KI as catalyst, for 31 hours. The precipitated solid is filtered off. Mother liquor is diluted with water and the semisolid oily residue separated is repeatedly extracted with toluene. The organic layers are collected and dried. The residue is dissolved in EtOH and the solution is acidified with 6N alcoholic HCl.

A solid precipitates, said solid is filtered off, and dissolved in water. The resulting solution is alkalinized with concentrated NH$_3$. The reaction product precipitates as free base. The product is crystallized firstly from EtOH, then from ButOH. Yield 0,9 g; m.p. 215–218° C.

5-[2-(4-benzamidopiperidino)ethyl]4-(4-fluorophenyl)-1,3-dihydro-2H-imidazol-2-one: m.p. 218–220° C. (from EtOH);

4-(4-fluorophenyl)-1,3-dihydro-5-[2-(4-(2-methoxyphenyl)-1-piperazinyl)ethyl]-2H-imidazol-2-one: m.p. 213–214° C. (from EtOH);

4-(4-fluorophenyl)-1,3-dihydro-5-[2-(4-methyl-1-piperazinyl)ethyl]-2H-imidazol-2-one: m.p. 237–239° C. (from EtOH) are prepared according to the above process.

EXAMPLE 3

5-[2-(4-(2-oxo-benzimidazolinyl)piperidinyl)ethyl]-4-(4-fluorophenyl)-1,3-dihydro-2H-imidazol-2-one 3 g (0,012 mole) of 3-(2-chloroethyl)-4-(4-fluorophenyl)-1,3-dihydro-2H-imidazol-2-one (prepared as described in example 1) 2,7 g (0,012 mole) of 4-(2-oxo-1-benzimidazolinyl)piperidine, 1,5 g triethylamine, KI as catalyst, 30 ml DMF are placed in a closed glass-tube.

The mixture is heated at 80° C. for 35 hours. The solid is filtered off after cooling and the solution is poured in water.

The precipitated solid is crystallized from hot EtOH.

The crystallized solid, after drying, is suspended in EtOH and treated with an alcoholic HCl solution. The hydrochloride of the product is yielded: m.p. 252–256° C.

4-(4-fluorophenyl)-1,3-dihydro-5-[2-(4-phenyl-1-piperazinyl)ethyl]-2H-imidazol-2-one: m.p. 232–234° C. (from EtOH).

We claim:

1. A compound of general formula I

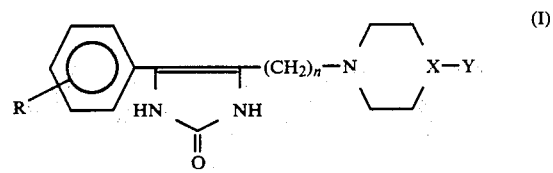

wherein:

R is an halogen atom, a straight or branched C$_1$–C$_4$ alkoxy group or a C$_1$–C$_4$ alkyl group;

n is an integer from 1 to 3;

X is a nitrogen atom forming a piperazine ring in which case Y may be a C$_1$–C$_4$ alkyl group unsubstituted or substituted by a hydroxy group; a phenyl group unsubstituted or substituted by one or more halogen atoms, C$_1$–C$_4$ alkoxy group or by hydroxy group;

or X is a CH group and Y is then hydrogen, phenyl, benzoyl, benzamido, 2-oxo-1-benzimidazolinyl groups unsubstituted or substitute by one or more halogen atoms or a pharmaceutically acceptable salt thereof.

2. A compound according to claim 1, where X is N and Y is methyl, ethyl, 2-hydroxyethyl, 2-hydroxypropyl, phenyl, 2-hydroxyphenyl or methoxyphenyl group.

3. A compound according to claim 1, wherein X is CH and Y is 2-oxo-1-benzimidazolinyl or benzamido group.

4. A compound according to claim 1 which is 4-(4-fluorophenyl)-1,3-dihydro-5-[2-(4-(2-methoxyphenyl)1-piperazinyl) ethyl]-2H-imidazol-2-one or a pharmaceutically acceptable salt thereof.

5. A pharmaceutical composition having antipsychotic, antidepressive and ansiolytic activity and useful in the prevention and therapy of hypertension, ischaemic cardiopathies, thrombosis and cerebral circulation disorders which comprises as the principal active ingredient an effective amount of a compound according to claim 1 in admixture with a pharmaceutically acceptable carrier.

6. A method of treating a patient having a central nervous or cardiovascular system disorder which comprises administering thereto an effective amount of a composition according to claim 5.

* * * * *

UNITED STATES PATENT AND TRADEMARK OFFICE
CERTIFICATE OF CORRECTION

PATENT NO. : 5,059,601

DATED : October 22, 1991

INVENTOR(S) : Aldo Salimbeni, et al

It is certified that error appears in the above-identified patent and that said Letters Patent is hereby corrected as shown below:

On the title page, item 30, "Jan. 25, 1989" should read

--Jan 26, 1989--.

Signed and Sealed this

Ninth Day of March, 1993

*Attest:*

STEPHEN G. KUNIN

*Attesting Officer*     Acting Commissioner of Patents and Trademarks